US009066985B2

(12) United States Patent
Packard et al.

(10) Patent No.: US 9,066,985 B2
(45) Date of Patent: Jun. 30, 2015

(54) FLUORINE-18 LABELED RHODAMINE DERIVATIVES FOR IMAGING WITH POSITRON EMISSION TOMOGRAPHY

(71) Applicant: Children's Medical Center Corporation, Boston, MA (US)

(72) Inventors: Alan B. Packard, Framingham, MA (US); Tobias K. Heinrich, Berlin (DE); S. Ted Treves, Wellesley, MA (US); Vijay Gottumukkala, Quincy, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 14/101,960

(22) Filed: Dec. 10, 2013

(65) Prior Publication Data

US 2014/0100377 A1 Apr. 10, 2014

Related U.S. Application Data

(63) Continuation of application No. 12/479,520, filed on Jun. 5, 2009, which is a continuation-in-part of application No. PCT/US2008/065300, filed on May 30, 2008.

(60) Provisional application No. 60/932,308, filed on May 30, 2007.

(51) Int. Cl.
*A61K 49/00* (2006.01)
*A61K 51/04* (2006.01)

(52) U.S. Cl.
CPC ............. *A61K 51/0421* (2013.01); *A61K 51/04* (2013.01)

(58) Field of Classification Search
None
See application file for complete search history.

(56) References Cited

U.S. PATENT DOCUMENTS

2007/0031328 A1* 2/2007 Kung ........................... 424/1.11

FOREIGN PATENT DOCUMENTS

EP 0468821 A1 1/1992
JP 2000344684 A 12/2000

OTHER PUBLICATIONS

T.K. Heinrich, S.T. Treves and A.B. Packard, Development of 18F-labeled rhodamine B derivatives for myocardial perfusion imaging with PET AMI/SMI Joint Molecular Imaging Conference, Providence, RI (2007).
Reungpatthanaphong, S. Dechsupa, J. Meesungnoen, C. Loetchutinat and S. Mankhetkorn, Rhodamine B as a mitochondrial probe for measurement and monitoring of mitochondrial membrane potential in drug-sensitive and resistant cells, J. Biochem. Biophys. Methods 57 (2003), pp. 1-16.
Vogel et al., Chem. Phys. Lett., 1988, 147, 452-460.
Gilissen, C., et al., "Synthesis of N-(2-[18F]fluoroethyl)-N'-methylthiourea : a hydrogen peroxide scavenger" J. Label. Compd. Radiopharm., 41(6): 491-502, 1998.
Jelinski, M., et al., "C-Terminal 18F-fluoroethylamidation exemplified on [Gly-OH9] oxytocin" J. Label. Compd. Radiopharm., 45(3): 217-229, 2002.
Lehel, Sz et al., "Synthesis of 5'-N-(2-[18F]Fluoroethyl)-carboxamidoadenosine: a Promising Tracer for Investigation of Adenosine Receptor System by PET Technique" J. Label. Compd. Radiopharm., 43: 807-815, 2000.
Lu, et al., "Efficient O- and N-(β-fluoroethylation)s with NCA [18F]β-fluoroethyl tosylate under microwave-enhanced conditions" J. Label. Compd. Radiopharm. 2004, 47: 289-97, 2004.
Madar, I. et al., "Charactrization of Uptake of the New PET Imaging Compound 18F-Fluorobenzyl Triphenyl Phosphonium in Dog Myocardium" J. Nucl. Med. 47: 1359-1366, 2006.
Madar, I. et al., "Assessment of Severity of Coronary Artery Stenosis in a Canine Model Using the PET agent 18F-Fluorobenzyl Triphenyl Phosphonium: Comparison with 99mTc-Tetrofosmin" J. Nucl. Med. 48:1021-1030, 2007.
Madar, I. et al., "18F-Fluorobenzyltriphenyl phosphonium PET detects area-specific apoptosis in the aging myocardium" Society of Nuclear Medicine, Annual Meeting Abstracts Abstract No. 562, 2007.
Ravert, H. et al., "Radiosynethesis of 3-[18F]fluoropropyl and 4-[18F]fluorobenzyl triarylphosphonium ions" J Label Compd Radiopharm 47:469-476, 2004.
Shoup, T. M. et al., "Evaluation of (4-[18F]Fluorophenyl)Triphenylphosphonium Ion as a Potential Myocardial Blood Flow Agent for PET" Abstract Book Supplement to J. Nucl. Med. Oral Presentation Abstract No. 178.
Studenov, A. et al., "Synthesis and properties of 18F-labeled potential myocardial blood flow tracers" Nucl. Med. Biol. 28: 683-693, 2001.
VanBrocklin, H. et al., "Hitrochondrial avid radioprobes. Preparation and evaluation of 7' (Z)'[125I]iodorotenone and 7' (Z)-[125I]iodorotenol" Nucl. Med. Biol. 34: 109-116, 2007.
Vora, M. et al., "In Vivo Studies of Unlabeled and Radioiodinated Rhodamine-123" Nucl. Med. Biol. 19(3):405-410, 1992.
Zhang, M-R., et al., "How to increase the reactivity of [18F]fluoroethyl bromide: [18F]fluoroethylation of amine, phenol and amide functional groups with [18F]FEtBr, [18F]FEtBr/NaI and [18F]FEtOTf" J. Label. Compd. Radiopharm., 46: 587-598 2003.
Harapanhalli, R. S., et al., "[125I/127I/131I]Iodorhodamine: Synthesis, Cellular Localization, and Biodistribution in Athymic Mice Bearing Human Tumor Xenographts and Comparison with [99mTc]Hexakis(2-methoxyisobutylisonitril)," Med. Chem. 41: 2111-2117 (1998).
Lu et al. J. Label. Compd. Radiopharm. 47: 289-297 (2004).
Madar, I. et al., J. Nucl. Med. 47(8):1359-1366 (2006).
Studenov, A. R., et al., "Synthesis and properties of 18F-labeled potential myocardial blood flow tracers," Nucl. Med. Biol., 28: 683-693 (2001).
VanBrocklin, H. et al., Nucl. Med. Biol. 34:109-116 (2007).
Vora M. M., et al., "In Vivo Studies of Unlabeled and Radioiodinated Rhodamine-123," Nucl. Med. Biol. 19(3):405-410 (1992).
Ferrieri, R., Handbook of Radiopharmaceuticals: Radiochemistry and Applications, pp. 229-282 (2003). "Production and application of synthetic precursors labeled with carbon-11 and fluorine-18."

\* cited by examiner

*Primary Examiner* — Michael G Hartley
*Assistant Examiner* — Sean R Donohue
(74) *Attorney, Agent, or Firm* — Nixon Peabody LLP

(57) ABSTRACT

The present invention is directed toward novel fluorine-18 labeled rhodamine dye derivatives and methods of making the same. The present invention is also directed toward methods of using novel fluorine-18 labeled rhodamine dye derivatives as positron emission tomography imaging agents and myocardial perfusion imaging agents.

12 Claims, 3 Drawing Sheets

Rhodamine B Fluoroethyl Ester

Rhodamine B Fluoropropyl Ester

Rhodamine B Fluorodiethyleneglycol Ester

FLUORINE-18 LABELED RHODAMINE DERIVATIVES FOR IMAGING WITH POSITRON EMISSION TOMOGRAPHY

CROSS REFERENCE TO RELATED APPLICATIONS

This application is a Continuation application of co-pending U.S. patent application Ser. No. 12/479,520 filed Jun. 5, 2009 which is a Continuation-in-Part of International PCT Application No. PCT/US2008/065300, filed May 30, 2008, which claims the benefit under 35 U.S.C. §119(e) to U.S. Provisional Application Ser. No. 60/932,308, filed May 30, 2007, the contents of each of which are incorporated herein by reference in their entireties.

FIELD OF THE INVENTION

The present disclosure relates to $^{18}$F-labeled dye compounds, methods of making the same, and their use for positron emission tomography imaging, particularly myocardial perfusion imaging, of a subject.

BACKGROUND OF THE INVENTION

Myocardial perfusion imaging (MPI) is a diagnostic technique useful for the detection and characterization of coronary artery disease. Perfusion imaging uses materials such as radioisotopes to identify areas of insufficient blood flow.

Radioisotopes are commonly used in contemporary medical imaging. One of the most important clinically-employed radioisotopes is technetium-99m ($^{99m}$Tc). Other radioisotopes, including halogens, such as $^{18}$F, $^{125}$I, $^{131}$I and $^{82}$Br, and isotopes of various metal radionuclides of lead, gallium, rhenium, rubidium, arsenic and copper, have also been explored as potential imaging agents. Medical imaging is used in a variety of medical applications, including imaging of the brain, tumors, and components of the cardiovascular system.

Perfusion agents are currently one of the most important tools for determining heart function. Tl-201, Tc-99-MIBI and Tc-99-tetrofosmin are in routine use for myocardial imaging at rest and after exercise. These agents are very useful but are not optimal. These tracers are single-photon imaging agents and the utility is limited by the properties of existing single-photon emission computed tomography (SPECT) imaging cameras and technology. Positron Emission Tomography (PET), however, has several advantages in comparison to SPECT including higher image resolution and more straightforward attenuation correction. Fluorine-18 is a positron-emitting radionuclide whose physical properties ($t_{1/2}$=110 min., 97% positron yield) are well suited to PET imaging, and the number of PET cameras and imaging centers are growing rapidly in response to the increased availability of $^{18}$F, particularly as [$^{18}$F]FDG (2-fluorodeoxyglucose).

Fluorine-18 is one of the most useful positron emitting radionuclides currently being used in clinical nuclear medicine diagnosis. For example, 2-[$^{18}$F]FDG (2-[$^{18}$F]-fluoro-2-deoxy-D-glucose) is the radiopharmaceutical of choice for the diagnosis of several cancers and brain disorders. This radiopharmaceutical produces superior high-resolution images and quantitative data about regional uptake by tissue. The 110-min half-life of $^{18}$F allows production and distribution of 2-[$^{18}$F]FDG to nuclear medicine facilities that do not have access to a cyclotron. The relatively long physical half-life of $^{18}$F also permits PET studies of moderately slow physiological process. Decay of $^{18}$F is largely by positron emission (97%), and the emitted positron is of relatively low energy (maximum 0.635 MeV) and thus has a short mean range (2.39 mm in water). Fluorine-18 is readily available from both particle accelerators and nuclear reactors using a wide variety of nuclear reactions, and can be produced at specific activities approaching the theoretical limit of 1.171×10$^9$ Ci/mmol.

Myocardial perfusion imaging (MPI) is extremely useful in the diagnosis of cardiac disease. PET (positron-emission tomography) MPI provides functional images of high quality that can be co-registered with [$^{18}$F]FDG images to delineate regions of infarct and ischemia. Short-lived compounds such as [$^{15}$O]H$_2$O, [$^{13}$N]NH$_3$, and $^{82}$Rb are well established PET MPI tracers, but PET centers without a cyclotron are limited to using $^{82}$Rb, which has significant limitations including high cost and high positron energy.

The present invention is directed to overcoming these and other deficiencies in the art.

SUMMARY OF THE INVENTION

According to one aspect of the invention there are provided novel fluorine-18 labeled rhodamine derivatives which are represented by formulas I and II:

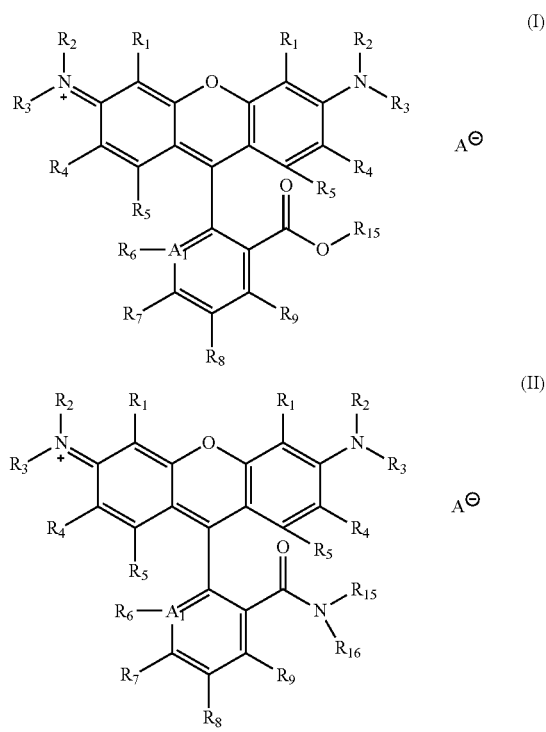

wherein $R_{10}$, $R_{11}$, $R_{12}$, $R_{13}$ and $R_{14}$ are each independently selected from the group consisting of hydrogen, substituted or unsubstituted alkyl, substituted or unsubstituted alkenyl, substituted or unsubstituted alkynyl, substituted or unsubstituted heterocycloalkyl, substituted or unsubstituted alkoxy, substituted or unsubstituted carbonyl, acylamino, halogen, halogen radioisotope, substituted or unsubstituted aryl, substituted or unsubstituted heteroaryl, substituted or unsubstituted amino, substituted or unsubstituted alkylamino, substituted or unsubstituted arylamino and isothiocyano;

wherein $R_2$ and $R_3$, taken together with the nitrogen atom to which they are attached, may optionally form a substituted or unsubstituted heterocyclic ring system;

$R_2$ and $R_{10}$, taken together with the atoms to which they are attached, may optionally form a 5- or 6-membered heterocyclic ring;

$R_2$ and $R_1$, taken together with the atoms to which they are attached, may optionally form a 5- or 6-membered heterocyclic ring; and $R_3$ and $R_4$, taken together with the atoms to which they are attached, may optionally form a 5- or 6-membered heterocyclic ring or a substituted or unsubstituted heterocyclic ring system;

$A_1$ is carbon or nitrogen, if $A_1$ is nitrogen, then $R_6$ is absent;

$R_6$ is absent or selected from the group consisting of hydrogen, substituted or unsubstituted alkyl, substituted or unsubstituted alkenyl, substituted or unsubstituted alkynyl, substituted or unsubstituted heterocycloalkyl, substituted or unsubstituted alkoxy, substituted or unsubstituted carbonyl, acylamino, halogen, halogen radioisotope, substituted or unsubstituted aryl, substituted or unsubstituted heteroaryl, substituted or unsubstituted amino, substituted or unsubstituted alkylamino, substituted or unsubstituted arylamino, isothiocyano;

$R_7$, $R_8$ and $R_9$ are each independently selected from the group consisting of hydrogen, substituted or unsubstituted alkyl, substituted or unsubstituted alkenyl, substituted or unsubstituted alkynyl, substituted or unsubstituted heterocycloalkyl, substituted or unsubstituted alkoxy, substituted or unsubstituted carbonyl, acylamino, halogen, halogen radioisotope, substituted or unsubstituted aryl, substituted or unsubstituted heteroaryl, substituted or unsubstituted amino, substituted or unsubstituted alkylamino, substituted or unsubstituted arylamino, isothiocyano;

$R_{15}$ is independently selected from the group consisting of $^{18}F$-labeled substituted or unsubstituted alkyl, $^{18}F$-labeled substituted or unsubstituted alkenyl, $^{18}F$-labeled substituted or unsubstituted alkynyl, $^{18}F$-labeled substituted or unsubstituted heterocycloalkyl, $^{18}F$-labeled substituted or unsubstituted alkoxy, $^{18}F$-labeled substituted or unsubstituted carbonyl, $^{18}F$-labeled acylamino, halogen radioisotope, $^{18}F$-labeled substituted or unsubstituted aryl, $^{18}F$-labeled substituted or unsubstituted heteroaryl, $^{18}F$-labeled substituted or unsubstituted amino, $^{18}F$-labeled substituted or unsubstituted alkylamino, $^{18}F$-labeled substituted or unsubstituted arylamino, $^{18}F$-labeled isothiocyano, and —$(CH_2CH_2O)_mCH_2CH_2{}^{18}F$, wherein m is 1-50;

$R_{16}$ is independently selected from the group consisting of hydrogen, substituted or unsubstituted alkyl, substituted or unsubstituted alkenyl, substituted or unsubstituted alkynyl, substituted or unsubstituted heterocycloalkyl, substituted or unsubstituted alkoxy, substituted or unsubstituted carbonyl, acylamino, halogen, halogen radioisotope, substituted or unsubstituted aryl, substituted or unsubstituted heteroaryl, substituted or unsubstituted amino, substituted or unsubstituted alkylamino, substituted or unsubstituted arylamino, isothiocyano; and A- is an anion.

In one embodiment, $R_{15}$ is $^{18}F$-labeled substituted or unsubstituted alkyl.

In one embodiment, $R_{15}$ is —$(CH_2)_nCH_2{}^{18}F$, wherein n is 1-5.

In one embodiment, $R_{15}$ is —$CH_2CH_2CH_2{}^{18}F$.

In one embodiment, $R_{15}$ is —$(CH_2CH_2O)_mCH_2CH_2{}^{18}F$, wherein m is 1-4.

In one embodiment, $R_{15}$ is —$CH_2CH_2OCH_2CH_2{}^{18}F$.

In one embodiment, $R_2$ and $R_3$ are alkyl; $R_1$, $R_4$, $R_5$, $R_6$, $R_7$, $R_8$, and $R_9$ are hydrogen; and $A_1$ is carbon.

In one embodiment, $R_2$ and $R_4$ are alkyl; $R_1$, $R_3$, $R_5$, $R_6$, $R_7$, $R_8$, and $R_9$ are hydrogen; and $A_1$ is carbon.

In one embodiment, $R_2$ is ethyl.

In one embodiment, $R_3$ is ethyl.

In one embodiment, $R_4$ is methyl.

In one embodiment, $R_1$, $R_2$, $R_3$, $R_4$, $R_5$, $R_6$, $R_7$, $R_8$, and $R_9$ are hydrogen; and $A_1$ is carbon.

In one embodiment, $R_3$ and $R_4$, taken together with the atoms to which they are attached, form a 6-membered heterocyclic ring and $R_2$ and $R_1$, taken together with the atoms to which they are attached, form a 6-membered heterocyclic ring.

In one embodiment, $R_4$ is methyl; and $R_2$ and $R_3$ are each independently hydrogen or alkyl.

In another aspect, the invention provides a method of imaging myocardial perfusion comprising: administering to a patient a compound of claims 1-16; and scanning the patient using diagnostic imaging.

Another aspect of the present invention is directed toward a composition including a fluorine-18 labeled rhodamine derivative according to formula I or II and a pharmaceutically acceptable carrier.

Another aspect of the present invention is directed toward a method of obtaining a positron emission image of a portion of a mammal including administering to a mammal a fluorine-18 labeled rhodamine derivative according to formula I or II and acquiring a positron emission image of a portion of a mammal.

In one embodiment, the mammal is a human.

In one embodiment, the portion of a mammal is the myocardium.

A further aspect of the present invention is directed toward a method of imaging myocardial perfusion including administering to a patient a fluorine-18 labeled rhodamine derivative according to formula I or II and scanning the patient using diagnostic imaging.

A further aspect of the present invention is directed toward use of a fluorine-18 labeled rhodamine derivative according to formula I or II for the production of an imaging agent for carrying out myocardial perfusion imaging.

A still further aspect of the present invention is directed toward use of a fluorine-18 labeled rhodamine derivative according to formula I or II in the manufacture of an imaging agent for carrying out positron-emission tomography.

DETAILED DESCRIPTION OF THE INVENTION

Figure 1:
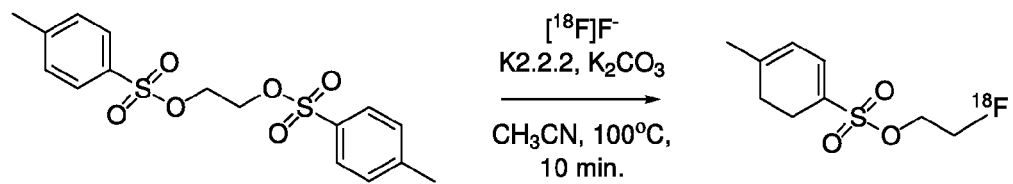
FIG. 1 is a reaction scheme illustrating the synthesis of 2-fluoroethyltosylate precursor.

Phenyl xanthene dyes, including rhodamine and rhodol dyes, are known. It is also known that certain dyes accumulate in mitochondria of living cells. Fluorine-18 radiolabeling of these dyes is not trivial due to the need for a suitable precursor and the appropriate conditions for radiolabeling. Here we describe such radiolabeled dyes and methods of their use as Positron Emission Tomography imaging agents.

The phenyl xanthene dyes comprise any fluorescein, rhodol or rhodamine ring system where the phenyl substituent at the 9-carbon ("the C9 phenyl ring") is a specific type of phenyl ring. For the purposes of this description, fluoresceins, rhodols and rhodamines are numbered in the following manner in formula (III):

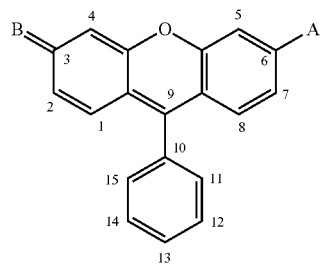

(III)

where A is either a hydroxyl or an amine group and B is a either an oxo or an imminium group. The C9 phenyl ring on the phenyl xanthene dye, whether substituted or unsubstituted, may be referred to as the "lower ring." The remainder of the molecule may be referred to as the "upper ring system."

The C9 phenyl ring is substituted at one or both of carbons C11 or C15 with a group selected from substituted or unsubstituted alkyl, heteroalkyl, alkoxy, halo, haloalkyl, amino, amido, alkylthio, carboxylic acid, ester, ether, cyano, isocyano, cyanato, mercaptocyanato, nitro, and sulfinyl. When both the C11 and C15 carbons are substituted, the substituents may be the same or different.

Any dye having this type of configuration is suitable. Preferred embodiments include rhodamine dyes wherein the C9 phenyl ring is substituted with a —COOH group. Preferred location for the —COOH substitution are C11 or C15. Examples of such rhodamine dyes are, but not limited to, rhodamine 590, rhodamine 110, rhodamine 101, rhodamine 575, and, preferably rhodamine 610. Further substitutions, such as nucleophilic substitution, may be made at any position as long as there remains room for an $^{18}$F.

Fluorine-18 is a positron-emitting radionuclide whose physical properties ($t_{1/2}$=110 min., 97% positron yield) are well suited to PET imaging, and the number of PET cameras and imaging centers are growing rapidly in response to the increased availability of $^{18}$F, particularly as [$^{18}$F]FDG (2-fluordeoxyglucose).

Fluorine-18 is one of the most useful positron emitting radionuclides currently being used in clinical nuclear medicine diagnosis. For example, 2-[$^{18}$F]FDG (2-[$^{18}$F]-fluoro-2-deoxy-D-glucose) is the radiopharmaceutical of choice for the diagnosis of several cancers and brain disorders. This radiopharmaceutical produces superior high-resolution images and quantitative data about regional uptake by tissue. The 110-min half-life of $^{18}$F allows production and distribution of 2-[$^{18}$F]FDG to nuclear medicine facilities that do not have access to a cyclotron. The relatively long physical half-life of $^{18}$F also permits PET studies of moderately slow physiological process. Decay of $^{18}$F is largely by positron emission (97%), and the emitted positron is of relatively low energy (maximum 0.635 MeV) and thus has a short mean range (2.39 mm in water). Fluorine-18 is readily available from both particle accelerators and nuclear reactors using a wide variety of nuclear reactions, and can be produced at specific activities approaching the theoretical limit of $1.171 \times 10^9$ Ci/mmol.

According to one aspect of the invention there are provided novel fluorine-18 labeled rhodamine derivatives which are represented by formulas I and II

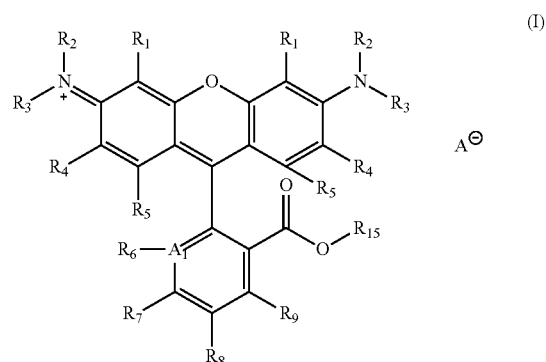

(I)

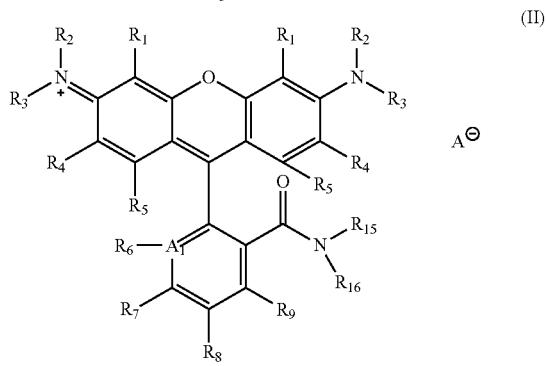

(II)

wherein $R_1$, $R_2$, $R_3$, $R_4$, and $R_5$, are each independently selected from the group consisting of hydrogen, substituted or unsubstituted alkyl, preferably having from 1 to 18 carbon atoms, substituted or unsubstituted alkenyl, preferably having from 2 to 18 carbon atoms, substituted or unsubstituted alkynyl, preferably having from 2 to 18 carbon atoms, substituted or unsubstituted heterocycloalkyl, substituted or unsubstituted alkoxy, substituted or unsubstituted carbonyl, acylamino, halogen, halogen radioisotope, substituted or unsubstituted aryl, substituted or unsubstituted heteroaryl, substituted or unsubstituted amino, substituted or unsubstituted alkylamino, substituted or unsubstituted arylamino, isothiocyano and a compound of formula III

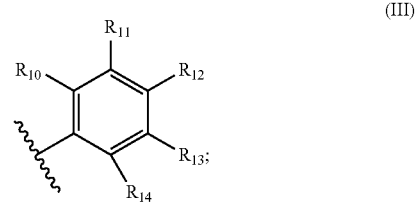

(III)

In formula III, $R_{10}$, $R_{11}$, $R_{12}$, $R_{13}$ and $R_{14}$ are each independently selected from the group consisting of hydrogen, substituted or unsubstituted alkyl, preferably having from 1 to 18 carbon atoms, substituted or unsubstituted alkenyl, preferably having from 2 to 18 carbon atoms, substituted or unsubstituted alkynyl, preferably having from 2 to 18 carbon atoms, substituted or unsubstituted heterocycloalkyl, substituted or unsubstituted alkoxy, substituted or unsubstituted carbonyl, acylamino, halogen, halogen radioisotope, substituted or unsubstituted aryl, substituted or unsubstituted heteroaryl, substituted or unsubstituted amino, substituted or unsubstituted alkylamino, substituted or unsubstituted arylamino and isothiocyano; IP In formulas I and II, $R_2$ and $R_3$, taken together with the nitrogen atom to which they are attached, can form a substituted or unsubstituted heterocyclic ring system, such as, for example, substituted and unsubstituted morpholines, pyrrolidines, and piperidines;

$R_2$ and $R_{10}$, taken together with the atoms to which they are attached can form a 5- or 6-membered heterocyclic ring such as, for example, indoline or tetrahydroquinoline;

$R_2$ and $R_1$ taken together with the atoms to which they are attached, can form a substituted or unsubstituted heterocyclic ring system, such as, for example, substituted and unsubstituted morpholines, pyrrolidines, and piperidines; or $R_3$ and $R_4$, taken together with the atoms to which they are attached, can form a substituted or unsubstituted heterocyclic ring system, such as, for example, substituted and unsubstituted morpholines, pyrrolidines, and piperidines, or a 5- or 6-membered heterocyclic ring such as, for example, indoline or tetrahydroquinoline.

$A_1$ is carbon or nitrogen, if $A_1$ is nitrogen, then $R_6$ is absent;

$R_6$ is absent or selected from the group consisting of hydrogen, substituted or unsubstituted alkyl, preferably having from 1 to 18 carbon atoms, substituted or unsubstituted alkenyl, preferably having from 2 to 18 carbon atoms, substituted or unsubstituted alkynyl, preferably having from 2 to 18 carbon atoms, substituted or unsubstituted heterocycloalkyl, substituted or unsubstituted alkoxy, substituted or unsubstituted carbonyl, acylamino, halogen, halogen radioisotope, substituted or unsubstituted aryl, substituted or unsubstituted heteroaryl, substituted or unsubstituted amino, substituted or unsubstituted alkylamino, substituted or unsubstituted arylamino and isothiocyano;

$R_7$, $R_8$ and $R_9$ are each independently selected from the group consisting of hydrogen, substituted or unsubstituted alkyl, preferably having from 1 to 18 carbon atoms, substituted or unsubstituted alkenyl, preferably having from 2 to 18 carbon atoms, substituted or unsubstituted alkynyl, preferably having from 2 to 18 carbon atoms, substituted or unsubstituted heterocycloalkyl, substituted or unsubstituted alkoxy, substituted or unsubstituted carbonyl, acylamino, halogen, halogen radioisotope, substituted or unsubstituted aryl, substituted or unsubstituted heteroaryl, substituted or unsubstituted amino, substituted or unsubstituted alkylamino, substituted or unsubstituted arylamino and isothiocyano;

$R_{15}$ is independently selected from the group consisting of hydrogen, substituted or unsubstituted alkyl, preferably having from 1 to 18 carbon atoms, substituted or unsubstituted alkenyl, preferably having from 2 to 18 carbon atoms, substituted or unsubstituted alkynyl, preferably having from 2 to 18 carbon atoms, substituted or unsubstituted heterocycloalkyl, substituted or unsubstituted alkoxy, substituted or unsubstituted carbonyl, acylamino, halogen, halogen radioisotope, substituted or unsubstituted aryl, substituted or unsubstituted heteroaryl, substituted or unsubstituted amino, substituted or unsubstituted alkylamino, substituted or unsubstituted arylamino and isothiocyano;

$R_{16}$ is independently selected from the group consisting of hydrogen, substituted or unsubstituted alkyl, preferably having from 1 to 18 carbon atoms, substituted or unsubstituted alkenyl, preferably having from 2 to 18 carbon atoms, substituted or unsubstituted alkynyl, preferably having from 2 to 18 carbon atoms, substituted or unsubstituted heterocycloalkyl, substituted or unsubstituted alkoxy, substituted or unsubstituted carbonyl, acylamino, halogen, halogen radioisotope, substituted or unsubstituted aryl, substituted or unsubstituted heteroaryl, substituted or unsubstituted amino, substituted or unsubstituted alkylamino, substituted or unsubstituted arylamino and isothiocyano;

A- is an anion; and at least one of the $R_1$-$R_{16}$ substituents is labeled with $^{18}F$.

A- is any anion known in the art, such as arsenide, azide, bromide, chloride, fluoride, hydride, iodine, nitride, oxide, phosphide, sulfide, or peroxide, may be used as the anion.

In one embodiment, the invention provides a compound comprising an $^{18}F$ labeled rhodamine derivative according to formula I or II:

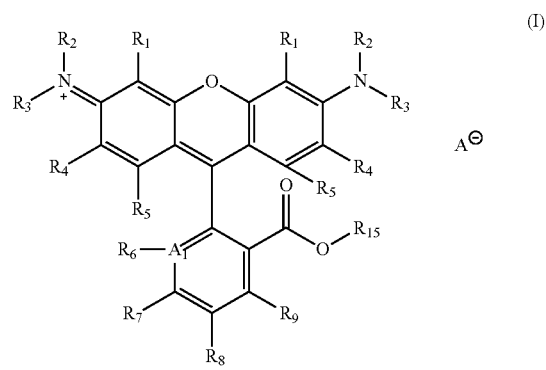

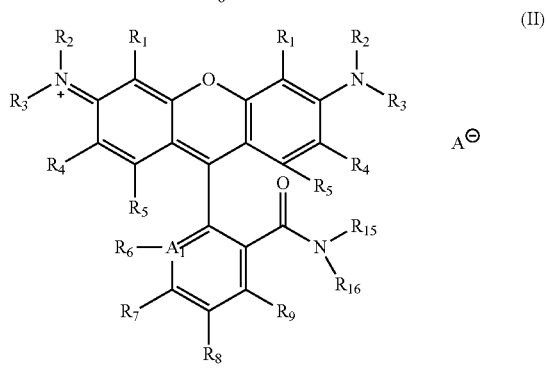

wherein $R_1$, $R_2$, $R_3$, $R_4$, and $R_5$ are each independently selected from the group consisting of hydrogen, alkyl, substituted alkyl, alkenyl, substituted alkenyl, heterocycloalkyl, substituted heterocycloalkyl, alkoxy, substituted alkoxy, substituted carbonyl, acylamino, halogen, and a compound of formula III

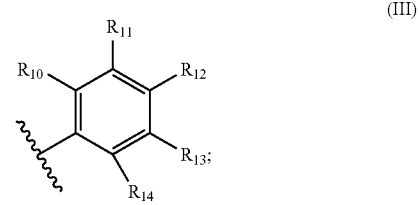

wherein $R_{10}$, $R_{11}$, $R_{12}$, $R_{13}$ and $R_{14}$ are each independently selected from the group consisting of hydrogen, alkyl, substituted alkyl, alkenyl, substituted alkenyl, heterocycloalkyl, substituted heterocycloalkyl, alkoxy, substituted alkoxy, substituted carbonyl, halogen, aryl, substituted aryl, heteroaryl, substituted heteroaryl, amino, substituted amino, alkylamino, substituted alkylamino, arylamino and substituted arylamino;

wherein $R_2$ and $R_3$, taken together with the nitrogen atom to which they are attached, may optionally form a substituted or unsubstituted heterocyclic ring system;

$R_2$ and $R_{10}$, taken together with the atoms to which they are attached, may optionally form a 5- or 6-membered heterocyclic ring;

$R_2$ and $R_1$, taken together with the atoms to which they are attached, may optionally form a 5- or 6-membered heterocyclic ring; and $R_3$ and $R_4$, taken together with the atoms to which they are attached, may optionally form a 5- or 6-membered heterocyclic ring or a substituted or unsubstituted heterocyclic ring system;

$A_1$ is carbon or nitrogen;

$R_6$ is absent or selected from the group consisting of hydrogen, alkyl, substituted alkyl, alkenyl, substituted alkenyl, heterocycloalkyl, substituted heterocycloalkyl, alkoxy, substituted alkoxy, substituted carbonyl, halogen, aryl, substituted aryl, heteroaryl, substituted heteroaryl, amino, substituted amino, alkylamino, substituted alkylamino, arylamino, substituted arylamino, and isothiocyano;

$R_7$, $R_8$ and $R_9$ are each independently selected from the group consisting of hydrogen, alkyl, substituted alkyl, alkenyl, substituted alkenyl, heterocycloalkyl, substituted heterocycloalkyl, alkoxy, substituted alkoxy, substituted carbonyl, halogen, aryl, substituted aryl, heteroaryl, substituted heteroaryl, amino, substituted amino, alkylamino, substituted alkylamino, arylamino, substituted arylamino, and isothiocyano;

$R_{15}$ is independently selected from the group consisting of hydrogen, alkyl, substituted alkyl, alkenyl, substituted alkenyl, heterocycloalkyl, substituted heterocycloalkyl, alkoxy, substituted alkoxy, aryl, substituted aryl, heteroaryl, substituted heteroaryl, amino, substituted amino, alkylamino, substituted alkylamino, arylamino, and substituted arylamino;

$R_{16}$ is independently selected from the group consisting of hydrogen, alkyl, substituted alkyl, alkenyl, substituted alkenyl, heterocycloalkyl, substituted heterocycloalkyl, alkoxy, substituted alkoxy, aryl, substituted aryl, heteroaryl, substituted heteroaryl, amino, substituted amino, alkylamino, substituted alkylamino, arylamino, and substituted arylamino; A- is an anion; and wherein at least one of the $R_1$-$R_{16}$ substituents is labeled with $^{18}F$.

In certain embodiments, the $^{18}F$ is present on the $R_{15}$ substituent.

In certain embodiments, when both $R_{15}$ and $R_{16}$ are present, the $^{18}F$ is present on both the $R_{15}$ and $R_{16}$ substituent.

In certain embodiments, the $R_{15}$ substituent is labeled with $^{18}F$ and at least one of the $R_1$-$R_{14}$ substituents is labeled with $^{18}F$.

In certain embodiment, when both $R_{15}$ and $R_{16}$ are present, both the $R_{15}$ and $R_{16}$ are labeled with $^{18}F$ and at least one of the $R_1$-$R_{14}$ substituents is labeled with $^{18}F$.

In certain embodiments, $R_2$ and $R_3$ are alkyl; $R_1$, $R_4$, $R_5$, $R_6$, $R_7$, $R_8$, and $R_9$ are hydrogen; and $A_1$ is carbon. In certain embodiments, $R_2$ is ethyl and/or $R_3$ is ethyl.

In other embodiments, $R_2$ and $R_4$ are alkyl; $R_1$, $R_3$, $R_5$, $R_6$, $R_7$, $R_8$, and $R_9$ are hydrogen; and $A_1$ is carbon. In certain embodiments, $R_2$ is ethyl and/or $R_4$ is methyl.

In yet other embodiments, $R_1$, $R_2$, $R_3$, $R_4$, $R_5$, $R_6$, $R_7$, $R_8$, and $R_9$ are hydrogen; and $A_1$ is carbon.

In certain embodiments, $R_3$ and $R_4$ taken together with the atoms to which they are attached form a 6-membered heterocyclic ring and $R_2$ and $R_1$ taken together with the atoms to which they are attached form a 6-membered heterocyclic ring.

In other embodiments, $R_4$ is methyl; and $R_2$ and $R_3$ are each independently hydrogen or alkyl.

In one embodiment, $R_{15}$ is independently selected from the group consisting of $^{18}F$, $^{18}F$-labeled substituted or unsubstituted alkyl, preferably having from 1 to 18 carbon atoms, $^{18}F$-labeled substituted or unsubstituted alkenyl, preferably having from 2 to 18 carbon atoms, $^{18}F$-labeled substituted or unsubstituted alkynyl, preferably having from 2 to 18 carbon atoms, $^{18}F$-labeled substituted or unsubstituted heterocycloalkyl, $^{18}F$-labeled substituted or unsubstituted alkoxy, $^{18}F$-labeled substituted or unsubstituted carbonyl, $^{18}F$-labeled acylamino, halogen radioisotope, $^{18}F$-labeled substituted or unsubstituted aryl, $^{18}F$-labeled substituted or unsubstituted heteroaryl, $^{18}F$-labeled substituted or unsubstituted amino, $^{18}F$-labeled substituted or unsubstituted alkylamino, $^{18}F$-labeled substituted or unsubstituted arylamino, $^{18}F$-labeled isothiocyano and $-(CH_2CH_2O)_mCH_2CH_2{}^{18}F$, wherein m is 1-50.

In one embodiment, in the $^{18}F$-labeled alkyl, $^{18F}$-labeled alkenyl, $^{18}F$-labeled alkynyl or $^{18}F$-labeled aryl at least one carbon has been replaced by a heteroatom.

In one embodiment, $R_{15}$ is $^{18}F$-labeled substituted or unsubstituted alkyl.

In one embodiment, $R_{15}$ is $-(CH_2)_nCH_2{}^{18}F$, wherein n is 0-17, preferably n is 1-10, more preferably n is 1-5.

In one embodiment, $R_{15}$ is $-CH_2{}^{18}F$.
In one embodiment, $R_{15}$ is $-CH_2CH_2{}^{18}F$.
In one embodiment, $R_{15}$ is $-CH_2CH_2CH_2CH_2{}^{18}F$.
In one embodiment, $R_{15}$ is $-CH_2CH_2CH_2CH_2CH_2{}^{18}F$.
In one embodiment, $R_{15}$ is $-CH_2CH_2CH_2CH_2CH_2CH_2{}^{18}F$.
In one preferred embodiment, $R_{15}$ is $-CH_2CH_2CH_2{}^{18}F$.
In one embodiment, $R_{15}$ is a $^{18}F$-labeled polyethylene glycol, e.g. 2K-, 5K-, 10K-, 12K-, 15K-PEG.

In one embodiment, $R_{15}$ is $-(CH_2CH_2O)_mCH_2CH_2{}^{18}F$, wherein m is 1-50, preferably m is 1-25, more preferably m is 1-10, and most preferably m is 1-4.

In one preferred embodiment, $R_{15}$ is $-CH_2CH_2OCH_2CH_2{}^{18}F$.

Another aspect of the present invention is directed toward a composition including a fluorine-18 labeled rhodamine derivative according to formula I or II and a pharmaceutically acceptable carrier.

As used herein, the term "acceptable pharmaceutical carrier" includes material, composition or vehicle, such as a liquid or solid filler, diluent, excipient, solvent or encapsulating material, involved in maintaining the agent in a deliverable form or in carrying or transporting the active agent from one organ, or portion of the body, to another organ, or portion of the body. Each carrier must be "acceptable" in the sense of being compatible with the other ingredients of the formulation and not injurious to the subject.

Some examples of materials which can serve as acceptable pharmaceutical carriers include, but are not limited to, (1) sugars, such as lactose, glucose, saccharin and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as dicalcium phosphate, cocoa butter and suppository waxes; (9) oils, such as peanut oil, cottonseed oil, safflower oil, sesame oil, olive oil, corn oil and soybean oil; (10) glycols, such as proplene glycol; (11) polyols, such as glycerine, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solution; (21) acacia; (22) lubricants, such as magnesium stearate and sodium lauryl sulfate; (23) preservatives, such as methyl and propylparabens; (24) dyes; (25) wetting agents; (26) emulsifiers; (27) coloring agents; (28) release agents; (29) coating agents; (30) flavoring agents; (31) perfuming agents; (32) sweetening agents; (33) antioxidants, such as ascorbic acid, cysteine hydrochloride, sodium bisulfate, sodium metabisulfite, ascorbyl palmitate, butylated hydroxyanisole, citric acid, ethylenediamine tetraacetic acid (EDTA), sorbitol, tartaric acid, phosphoric acid, and the like; and (24) other non-toxic compatible substances employed in pharmaceutical formulations.

Another aspect of the present invention is directed toward a method of obtaining a positron emission image of a portion of a mammal including administering to a mammal a fluorine-18 labeled rhodamine derivative according to formula I or II and acquiring a positron emission image of a portion of a mammal. The mammal may be a human. The portion of the mammal may be the myocardium.

A further aspect of the present invention is directed toward a method of imaging myocardial perfusion including administering to a patient a fluorine-18 labeled rhodamine derivative according to formula I or II and scanning the patient using diagnostic imaging.

A further aspect of the present invention is directed toward use of a fluorine-18 labeled rhodamine derivative according to formula I or II for the production of an imaging agent for carrying out myocardial perfusion imaging.

A still further aspect of the present invention is directed toward use of a fluorine-18 labeled rhodamine derivative according to formula I or II in the manufacture of an imaging agent for carrying out positron-emission tomography.

In one aspect the invention provides a compound comprising an $^{18}$F labeled rhodamine derivative according to formula I or II:

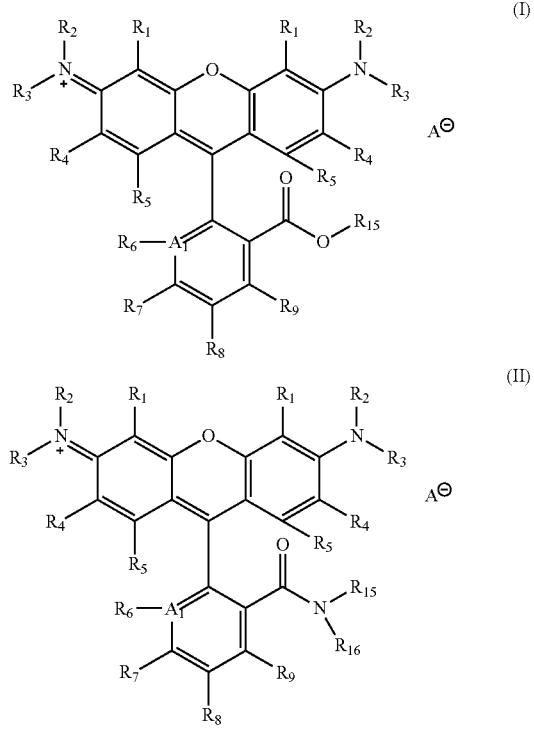

wherein $R_1$, $R_2$, $R_3$, $R_4$, and $R_5$ are each independently selected from the group consisting of hydrogen, substituted or unsubstituted alkyl, substituted or unsubstituted alkenyl, substituted or unsubstituted alkynyl, substituted or unsubstituted heterocycloalkyl, substituted or unsubstituted alkoxy, substituted or unsubstituted carbonyl, acylamino, halogen, halogen radioisotope, substituted or unsubstituted aryl, substituted or unsubstituted heteroaryl, substituted or unsubstituted amino, substituted or unsubstituted alkylamino, substituted or unsubstituted arylamino, isothiocyano and a compound of formula III

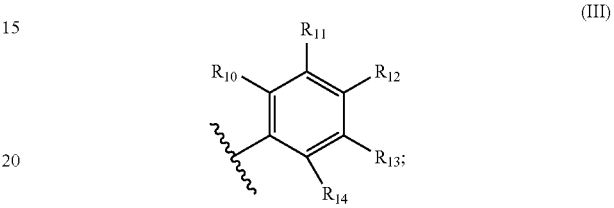

wherein $R_{10}$, $R_{11}$, $R_{12}$, $R_{13}$ and $R_{14}$ are each independently selected from the group consisting of hydrogen, substituted or unsubstituted alkyl, substituted or unsubstituted alkenyl, substituted or unsubstituted alkynyl, substituted or unsubstituted heterocycloalkyl, substituted or unsubstituted alkoxy, substituted or unsubstituted carbonyl, acylamino, halogen, halogen radioisotope, substituted or unsubstituted aryl, substituted or unsubstituted heteroaryl, substituted or unsubstituted amino, substituted or unsubstituted alkylamino, substituted or unsubstituted arylamino and isothiocyano;

wherein $R_2$ and $R_3$, taken together with the nitrogen atom to which they are attached, may optionally form a substituted or unsubstituted heterocyclic ring system;

$R_2$ and $R_{10}$, taken together with the atoms to which they are attached, may optionally form a 5- or 6-membered heterocyclic ring;

$R_2$ and $R_1$, taken together with the atoms to which they are attached, may optionally form a 5- or 6-membered heterocyclic ring; and $R_3$ and $R_4$, taken together with the atoms to which they are attached, may optionally form a 5- or 6-membered heterocyclic ring or a substituted or unsubstituted heterocyclic ring system;

$A_1$ is carbon or nitrogen, if $A_1$ is nitrogen, then $R_6$ is absent;

$R_6$ is absent or selected from the group consisting of hydrogen, substituted or unsubstituted alkyl, substituted or unsubstituted alkenyl, substituted or unsubstituted alkynyl, substituted or unsubstituted heterocycloalkyl, substituted or unsubstituted alkoxy, substituted or unsubstituted carbonyl, acylamino, halogen, halogen radioisotope, substituted or unsubstituted aryl, substituted or unsubstituted heteroaryl, substituted or unsubstituted amino, substituted or unsubstituted alkylamino, substituted or unsubstituted arylamino, isothiocyano;

$R_7$, $R_8$ and $R_9$ are each independently selected from the group consisting of hydrogen, substituted or unsubstituted alkyl, substituted or unsubstituted alkenyl, substituted or unsubstituted alkynyl, substituted or unsubstituted heterocycloalkyl, substituted or unsubstituted alkoxy, substituted or unsubstituted carbonyl, acylamino, halogen, halogen radioisotope, substituted or unsubstituted aryl, substituted or unsubstituted heteroaryl, substituted or unsubstituted amino, substituted or unsubstituted alkylamino, substituted or unsubstituted arylamino, isothiocyano;

R$_{15}$ is independently selected from the group consisting of $^{18}$F-labeled substituted or unsubstituted alkyl, $^{18}$F-labeled substituted or unsubstituted alkenyl, $^{18}$F-labeled substituted or unsubstituted alkynyl, $^{18}$F-labeled substituted or unsubstituted heterocycloalkyl, $^{18}$F-labeled substituted or unsubstituted alkoxy, $^{18}$F-labeled substituted or unsubstituted carbonyl, $^{18}$F-labeled acylamino, halogen radioisotope, $^{18}$F-labeled substituted or unsubstituted aryl, $^{18}$F-labeled substituted or unsubstituted heteroaryl, $^{18}$F-labeled substituted or unsubstituted amino, $^{18}$F-labeled substituted or unsubstituted alkylamino, $^{18}$F-labeled substituted or unsubstituted arylamino, $^{18}$F-labeled isothiocyano, and —(CH$_2$CH$_2$O)$_m$CH$_2$CH$_2$$^{18}$F, wherein m is 1-50;

R$_{16}$ is independently selected from the group consisting of hydrogen, substituted or unsubstituted alkyl, substituted or unsubstituted alkenyl, substituted or unsubstituted alkynyl, substituted or unsubstituted heterocycloalkyl, substituted or unsubstituted alkoxy, substituted or unsubstituted carbonyl, acylamino, halogen, halogen radioisotope, substituted or unsubstituted aryl, substituted or unsubstituted heteroaryl, substituted or unsubstituted amino, substituted or unsubstituted alkylamino, substituted or unsubstituted arylamino, isothiocyano; and A- is an anion.

DEFINITIONS

The term "alkyl" as used herein refers to saturated straight-chain, branched-chain or cyclic hydrocarbon radicals. Examples of alkyl radicals include, but are not limited to, methyl, ethyl, propyl, isopropyl, n-butyl, tert-butyl, neopentyl, n-hexyl, cyclohexyl, n-octyl, n-decyl, n-dodecyl and n-hexadecyl radicals.

The term "alkenyl" as used herein refers to unsaturated straight-chain, branched-chain or cyclic hydrocarbon radicals having at least one carbon-carbon double bond. Examples of alkenyl radicals include, but are not limited to, allyl, butenyl, hexenyl and cyclohexenyl radicals.

The term "alkynyl" as used herein refers to unsaturated hydrocarbon radicals having at least one carbon-carbon triple bond. Representative alkynyl groups include, but are not limited to, ethynyl, 1-propynyl, 1-butyryl, isopentynyl, 1,3-hexadiynyl, n-hexynyl, 3-pentynyl, 1-hexen-3-ynyl and the like.

The terms "halo" and "halogen", as used herein, refer to an atom selected from fluorine, chlorine, bromine and iodine. The term "halogen radioisotope" refers to a radionuclide of an atom selected from fluorine, chlorine, bromine and iodine.

The term "aryl," as used herein, refers to a mono-, bicyclic, or tricyclic carbocyclic ring system having one, two or three aromatic rings including, but not limited to, phenyl, naphthyl, anthryl, azulyl, tetrahydronaphthyl, indanyl, indenyl and the like.

The term "heteroaryl," as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "heterocycloalkyl," as used herein, refers to a non-aromatic 3-, 4-, 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "carbonyl" as used herein refers to a carbonyl group, attached to the parent molecular moiety through the carbon atom, this carbon atom also bearing a hydrogen atom, or in the case of a "substituted carbonyl" a substituent as described in the definition of "substituted" below.

The term "acyl" as used herein refers to groups containing a carbonyl moiety. Examples of acyl radicals include, but are not limited to, formyl, acetyl, propionyl, benzoyl and naphthoyl.

The term "alkoxy", as used herein, refers to a substituted or unsubstituted alkyl, alkenyl or heterocycloalkyl group, as previously defined, attached to the parent molecular moiety through an oxygen atom. Examples of alkoxy radicals include, but are not limited to, methoxy, ethoxy, propoxy, isopropoxy, n-butoxy, tert-butoxy, neopentoxy and n-hexoxy.

The term "aryloxy" as used herein refers to a substituted or unsubstituted aryl or heteroaryl group, as previously defined, attached to the parent molecular moiety through an oxygen atom. Examples of aryloxy include, but are not limited to, phenoxy, p-methylphenoxy, naphthoxy and the like.

The term "alkylamino", as used herein, refers to a substituted or unsubstituted alkyl, alkenyl or heterocycloalkyl group, as previously defined, attached to the parent molecular moiety through a nitrogen atom. Examples of alkylamino radicals include, but are not limited to, methylamino, ethylamino, hexylamino and dodecylamino.

The term "arylamino", as used herein, refers to a substituted or unsubstituted aryl or heteroaryl group, as previously defined, attached to the parent molecular moiety through a nitrogen atom.

The term "substituted" as used herein in phrases such as "substituted alkyl", "substituted alkenyl", "substituted aryl", "substituted heteroaryl", "substituted heterocycloalkyl", "substituted carbonyl", "substituted alkoxy", "substituted acyl", "substituted amino", "substituted aryloxy", "substituted amido", and the like, refers to independent replacement of one or more of the hydrogen atoms on the substituted moiety with substituents independently selected from, but not limited to, alkyl, alkenyl, heterocycloalkyl, alkoxy, aryloxy, hydroxy, amino, amido, alkylamino, arylamino, cyano, halo, mercapto, nitro, carbonyl, acyl, aryl and heteroaryl groups.

The term "substituted" as used herein in phrases such as "substituted nitrogen", "substituted oxygen" and "substituted sulfur" refers to nitrogen, oxygen or sulfur substituted with alkyl, aryl, or heteroaryl groups. Examples include, but are not limited to, alkyl and aryl ethers such as methoxy, ethoxy or phenoxy; alkyl or aryl thioethers such as thiomethoxy, thioethoxy and thiophenyl; alkyl or aryl amines such as dimethyl amino, diethylamino, diphenylamino, phenylamino, and N-methyl-N-phenylamino.

The compounds according to the invention may be prepared by synthetic processes which are known to those skilled in the art, particularly in view of the state of the art and the specific preparatory examples provided below herein.

Phenyl xanthene dyes can be prepared as described in U.S. Patent Pub. No. US 2004/0242902. Rhodamine dyes are described in U.S. Patent Pub. No. US 2006/0293523, U.S. Patent Pub. No. US 2007/0048640, U.S. Pat. No. 4,647,675, U.S. Pat. No. 4,895,961, U.S. Pat. No. 4,602,263, U.S. Pat. No. 4,826,976, and U.S. Pat. No. 516,584.

Generally, symmetrical rhodamine dyes can be prepared in one step from 3',6'-dichlorofluorans by reacting two equivalents of an aromatic or aliphatic amine as described in U.S. Pat. No. 4,602,263, GB2311075 and DE81056. The unsymmetrical rhodamine dyes are then prepared by the selective monoalkylation of symmetrical rhodamines using sodium hydride in dimethyl sulfoxide as described in U.S. Pat. Nos. 4,602,263 and 4,826,976.

Alternatively these novel unsymmetrical rhodamines can be prepared by use of an alternate synthetic pathway in which one equivalent of an N-alkylaniline is reacted selectively with the 3',6'-dichlorofluoran using aluminum chloride as a catalyst to produce 3'-chloro-6'-N-alkyl-N-arylfluorans. These products are isolated and purified prior to reacting with a second equivalent of an aromatic or aliphatic amine. Zinc chloride is used as the catalyst for the second addition. DE139727 describes the selective addition of anilines to 3',6'-dichlorofluorans to produce 3'-chloro-6'-arylaminofluorans using a mixture of zinc chloride and zinc oxide at 160° C.

Unsymmetrical rhodamines can also be made from 2-benzoyl benzoic acid derivatives by condensation with 3-arylamino phenols or 3-alkylamino phenols as described in Chemistry and Applications of Leuco Dyes, pp. 180-191 R. Muthyala, Ed., Plenum Press, New York and London, 1997 and also U.S. Pat. Nos. 4,390,616 and 4,436,920.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages may mean±1%.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

EXAMPLES

Example 1

Synthesis of 2-$^{18}$F-fluoroethyl Ester of Rhodamine B

Preparation of precursor-2-$^{18}$F-fluorethyltosylate

Ethylenebistosylate is reacted with dry [$^{18}$F]fluoride, Kryptofix 2.2.2 (K2.2.2) and potassium carbonate in anhydrous acetonitrile at 100° C. for 10 min. in a Pierce "V-vial" to produce the 2-$^{18}$F-fluorethyltosylate in 80-85% yield. The product may be purified by solid-phase extraction or chromatographically (e.g., semi-preparative HPLC). See FIG. 1.

Preparation of 2-$^{18}$F-fluoroethyl ester of rhodamine B

Figure 2:
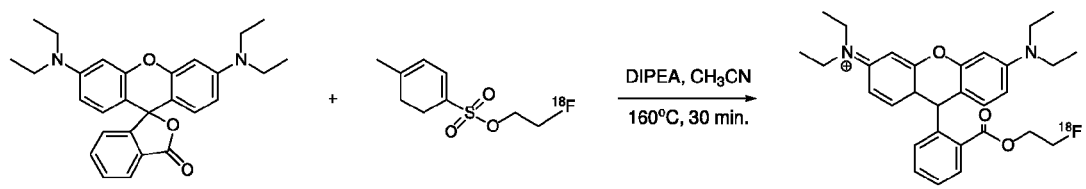
FIG. 2 is a reaction scheme illustrating reaction of 2-fluorethyltosylate with rhodamine lactone to form 2-fluoroethylester of rhodamine B.

2-$^{18}$F-fluorethyltosylate is added to a solution of rhodamine B lactone and diisopropylethylamine (DIPEA) in anhydrous acetonitrile and heated at 160° C. for 30 min. to produce the $^{18}$F-labeled fluoroethyl ester in ~35% yield. The product may be purified by solid-phase extraction or chromatographically (e.g., semi-preparative HPLC). See FIG. 2.

"One-Pot" Synthesis of 2-$^{18}$F-fluoroethyl ester of rhodamine B

Figure 3:
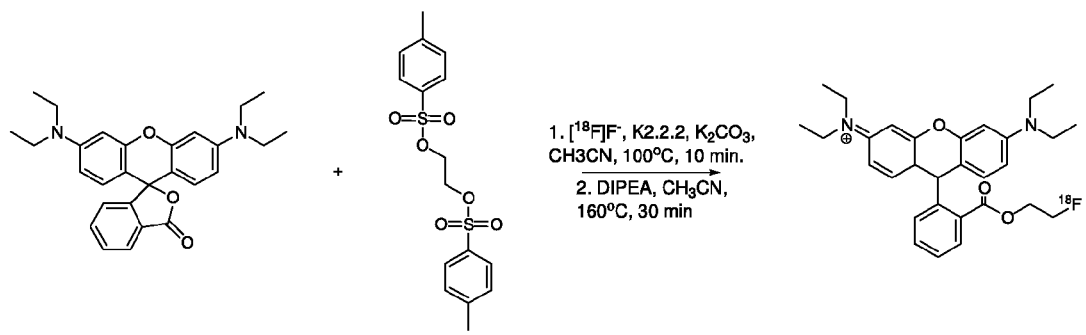
FIG. 3 is a reaction scheme illustrating the reaction performed by a two-step reaction in a single vessel, without isolation of the 2-fluoroethyltosylate precursor.

This reaction proceeds as outlined above but without isolation of the 2-$^{18}$F-fluorethyltosylate precursor. Ethylenebistosylate is reacted with dry [$^{18}$F]fluoride, Kryptofix 2.2.2 (K2.2.2) and potassium carbonate in anhydrous acetonitrile at 100° C. for 10 min. in a Pierce "V-vial" to produce the 2-$^{18}$F-fluorethyltosylate (80-85% yield). Rhodamine B lactone and DIPEA are added directly to the crude 2-$^{18}$F-fluorethyltosylate solution and heated for an additional 30 min. at 160° C. The final product, the 2-$^{18}$F-fluoroethylester of rhodamine B, is obtained in approximately 35% yield after purification by semi-preparative HPLC. The total reaction time is approximately 45 min. See FIG. 3. See Lu et al. *J. Label. Compd. Radiopharm.* 2004, 47: 289-97.

Example 2

Synthesis of 3-$^{18}$F-fluoropropyl Ester of Rhodamine B

The 3-$^{18}$F-fluoropropyl ester of rhodamine B is synthesized using the protocols outlined in Example 1 and starting with 1,3-bis-tosylate-propane. The final product, 3-$^{18}$F-fluoropropylester of rhodamine B, was obtained in approximately 28% yield after purification by semi-preparative HPLC.

Example 3

Synthesis of 5-$^{18}$F-fluoro-3-oxa-pentyl Ester of Rhodamine B

The $^{18}$F-labeled diethylene glycol ester of Rhodamine B is prepared using the protocols outlined in Example 1 and starting with 3-oxapentane-1,5-bistosylate. FluorodiethylenegycolTos (5-$^{18}$F-fluoro-3-oxa-pentyl-tosylate) was prepared from diethyleneglycol-ditosylate (123 mg, 0.39 mmol), potassium fluoride (25 mg, 0.43 mmol) and Kryptofix (200 mg, 0.53 mmol) in 5 mL of acetonitrile heated at 75° C. for 2 h. as described by Studenov, et al. Nuclear Medicine and Biology 28 (2001) 683-693. The product was obtained as oil in 60% yield. The FluorodiethylenegycolTos was reacted with rhodamine B lactone as outlined in Example 1. The final product, 5-$^{18}$F-fluoro-3-oxa-pentyl ester of rhodamine B, was obtained in approximately 27% yield after purification by semi-preparative HPLC.

Example 4

Figure 4:
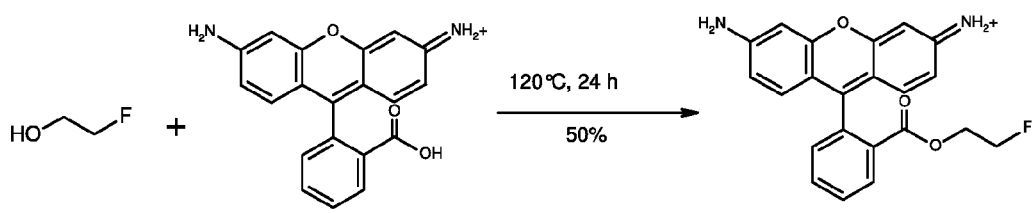
FIG. 4 is a reaction scheme illustrating the synthesis of 2-F-fluoroethyl ester of rhodamine 110 as cold reference compound for esters.

Synthesis of 2-F-fluoroethyl Ester of Rhodamine 110 as cold reference compound for esters Rhodamine 110 is heated in 2-fluoroethanol at 120° C. for 24 h and purified on C18 reversed phase silica gel to deliver the Fluoroethyl ester in 50% yield. See FIG. 4.

Example 5

Synthesis of 3-fluoropropyl Ester of Rhodamine B (FERhB) as cold reference compound for esters The nonradioactive 3-fluoropropyl ester of rhodamine B was prepared by transesterification of rhodamine B lactone with 3-fluoropropyl p-toluenesulfonate. 88.4 mg of rhodamine B lactone (0.2 mmol) were dissolved in 4 mL acetonitrile to which 55.5 mg 3-fluoropropyl p-toluenesulfonate (0.23 mmol, previously dissolved in 1 mL acetonitrile) and 0.178 mL (1 mmol) diisopropylethylamine were added. The solution was refluxed and the reaction was monitored by TLC. After 24 h, 50% of the rhodamine B lactone starting material had been converted to the 3-fluoropropyl ester, at which time the heating was discontinued, the reaction mixture was allowed to cool to room temperature, and then evaporated to dryness to give approx. 50 mg of crude product as a dark red oil. 10 mg of the crude product was purified by semi-preparative HPLC to provide 5 mg (50%) of purified FPRhB as a purple solid

Example 6

Synthesis of 5-fluoro-3-oxa-pentyl Ester of Rhodamine B (FERhB) as cold reference compound for esters The nonradioactive 5'-fluorodiethylenegycol ester of rhodamine B was prepared by transesterification of rhodamine B ketone with 5-fluoroethyleneglycol p-toluenesulfonate. 25 mg of 1 (0.056 mmol) were dissolved in 3 mL acetonitrile to which 17.5 mg 5-fluorodiethyleneglycol p-toluenesulfonate (0.067 mmol, previously dissolved in 2 mL acetonitrile) and 0.05 mL (0.294 mmol) diisopropylethylamine were added. The solution was refluxed and the reaction was monitored by HPLC. After 2 h, 60% of the rhodamine B lactone starting material had been converted to the 5-fluorodiethylenegycol ester, at which time the heating was discontinued, the reaction mixture was allowed to cool to room temperature, and then evaporated to dryness to give approx. 19 mg of crude product as dark red oil. 10 mg of the crude product was purified by semi-preparative HPLC to provide 7 mg (70%) of purified FEGRhB as a purple solid.

Example 7

Preparation of precursor-2-$^{18}$F-fluorethylamine for amide synthesis

Figure 5:
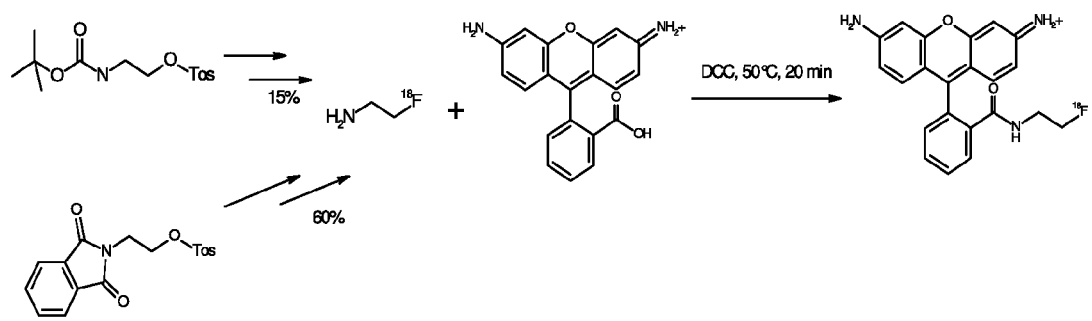
FIG. 5 is a reaction scheme illustrating the preparation of precursor-2-$^{18}F$-fluorethylamine and 2-$^{18}F$-fluoroethyl amide of rhodamine 110.

Fluoroethylamine was made according to literature starting either from (2-methoxy-ethyl)-carbamic acid tert-butyl ester or 2-(2-methoxy-ethyl)-isoindole-1,3-dione, which is reacted with dry [$^{18}$F]fluoride, Kryptofix 2.2.2 (K2.2.2) and potassium carbonate in anhydrous acetonitrile at 100° C. for 10 min. in a Pierce "V-vial" to produce the 2-$^{18}$F-fluorethylamine after cleavage of the protecting group in 15 respectively 60% radiochemical yield. The product may be purified by solid-phase extraction or HPLC. See FIG. 5.

Example 8

Preparation of 2-$^{18}$F-fluoroethyl amide of rhodamine 110

2-$^{18}$F-fluorethylamine is added to a solution of rhodamine 110 in Chloroform and dicyclohexyl carbodiimide is added also in Chloroform and stirred at 40° C. for 20 min. to produce the $^{18}$F-labeled fluoroethyl amide in ~25% yield. The product may be purified by solid-phase extraction or semipreparative. HPLC. See FIG. 5.

Example 9

Direct labeling of 2-$^{18}$F-fluoroethyl amide of rhodamine 110

Figure 6:
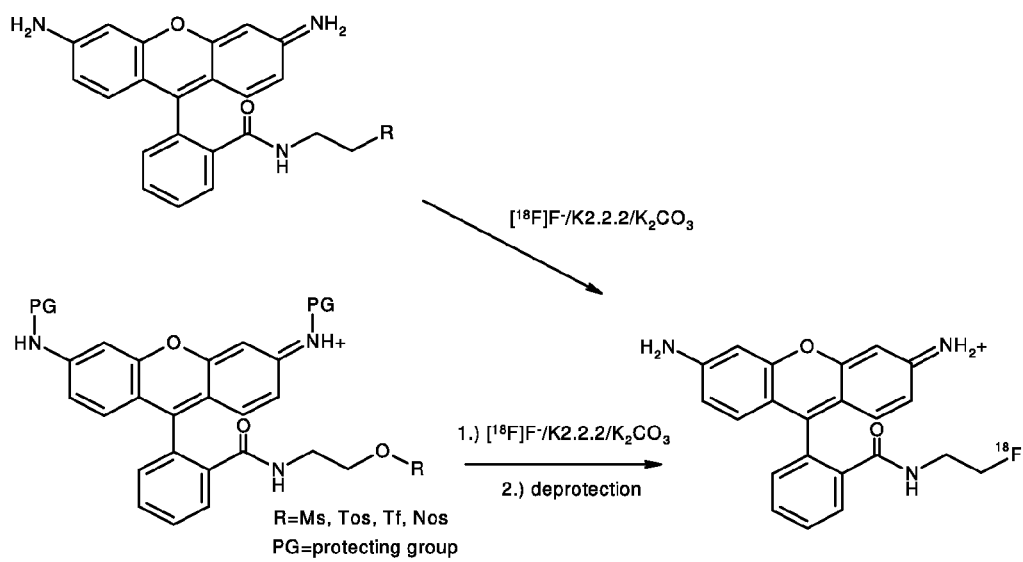
FIG. 6 is a reaction scheme illustrating the direct labeling of 2-$^{18}F$-fluoroethyl amide of rhodamine 110.
Figure 7:
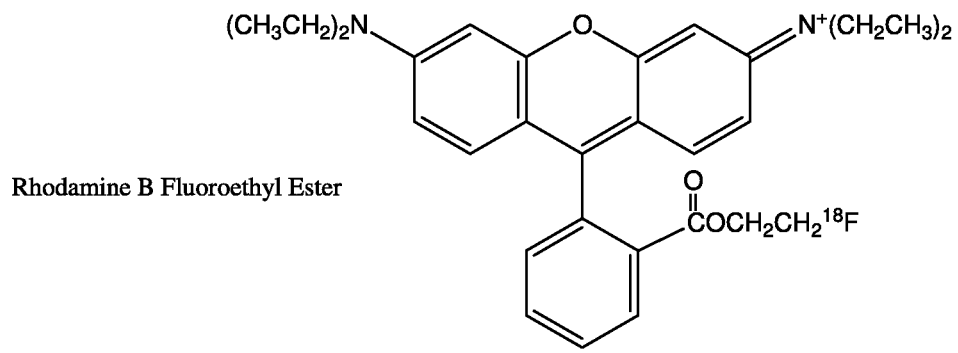
FIG. 7 shows of the $^{18}F$-labeled rhodamine B esters.
Figure 7:
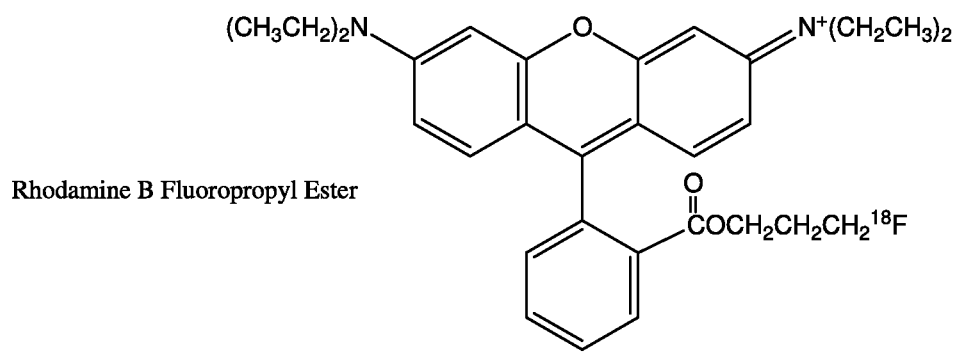
Figure 7:
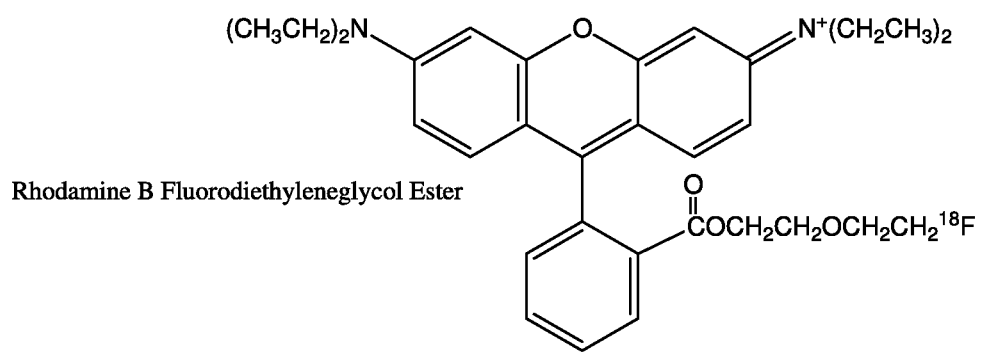

This reaction proceeds from a direct labeling precursor, e.g methanesulfonic acid benzoylamino-ethyl ester is reacted with dry [$^{18}$F]fluoride, Kryptofix 2.2.2 (K2.2.2) and potassium carbonate in anhydrous acetonitrile at 100° C. for 10 min. in a Pierce "V-vial" to produce the 2-$^{18}$F-fluoroethylamide (20-25% yield). See FIG. 6.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

All references disclosed herein are incorporated by reference in their entirety.

REFERENCES

1. Vora, M. et al., *Nucl. Med. Biol.* 19(3):405-410, 1992.
2. Studenov, A. et al., *Nucl. Med. Biol.* 28:683-693, 2001.
3. Madar, I. et al., *J. Nucl. Med.* 48(6):1021-1030, 2007.
4. Madar, I. et al., *J. Nucl. Med.* 47(8):1359-1366, 2006.
5. Ravert, H. et al., *J Label Compd Radiopharm* 47:469-476, 2004.
6. VanBrocklin, H. et al., *Nucl. Med. Biol.* 34:109-116, 2007.
7. Madar, I. et al., "$^{18}$F-Fluorobenzyltriphenyl phosphonium PET detects area-specific apoptosis in the aging myocardium" *Society of Nuclear Medicine, Annual Meeting Abstracts* Abstract No. 562, 2007.
8. Shoup, T. M. et al., "Evaluation of (4-[$^{18}$F]Fluorophenyl) Triphenylphosphonium Ion as a Potential Myocardial Blood Flow Agent for PET" *Abstract Book Supplement to J. Nucl. Med.* Oral Presentation Abstract No. 178.
9. Lu et al. *J. Label. Compd. Radiopharm.* 2004, 47: 289-97.
10. Gilissen, C., et al., *J. Label. Compd. Radiopharm.*, 41(6): 491-502 (1998).
11. Jelinski, M., et al., *J. Label. Compd. Radiopharm.*, 45(3): 217-229 (2002).
12. Lehel, Sz. et al., *J. Label. Compd. Radiopharm.*, 43(8): 807-815 (2000).
13. Zhang, M-R., et al., *J. Label. Compd. Radiopharm.*, 46: 587-598 (2003).

What is claimed is:

1. A compound comprising an $^{18}$F labeled rhodamine derivative according to formula I:

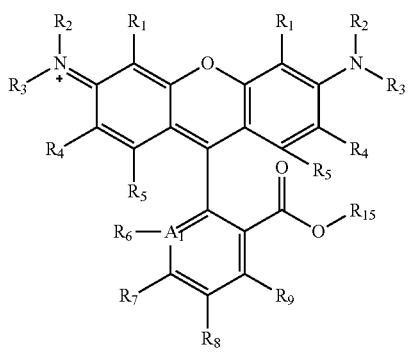

(I)

wherein $R_1$, $R_3$, and $R_5$ are hydrogen;
$R_2$ and $R_4$ are alkyl;
$A_1$ is carbon or nitrogen, if $A_1$ is nitrogen, then $R_6$ is absent;
$R_6$ is hydrogen;
$R_7$, $R_8$ and $R_9$ are hydrogen;
$R_{15}$ is —$(CH_2CH_2O)_m CH_2CH_2{}^{18}F$, wherein m is 1-50; and
A- is an anion.

2. The compound of claim 1, wherein $R_1$, $R_3$, $R_5$, $R_6$, $R_7$, $R_8$, and $R_9$ are hydrogen; and $A_1$ is carbon.

3. The compound of claim 1, wherein $R_2$ is ethyl.

4. The compound of claim 1, wherein $R_4$ is methyl.

5. The compound of claim 1, wherein $R_{15}$ is —$(CH_2CH_2O)_m CH_2CH_2{}^{18}F$, wherein m is 1-4.

6. The compound of claim 5, wherein $R_{15}$ is —$CH_2CH_2OCH_2CH_2{}^{18}F$.

7. The compound of claim 1, wherein $R_1$, $R_3$, $R_5$, $R_6$, $R_7$, $R_8$, and $R_9$ are hydrogen; $R_2$ is ethyl; $R_4$ is methyl; $R_{15}$ is —$CH_2CH_2OCH_2CH_2{}^{18}F$; and $A_1$ is carbon.

8. The compound of claim 1, wherein the compound is a myocardial positron imagining agent.

9. A pharmaceutical composition comprising a compound of claim 1 and a pharmaceutically acceptable carrier.

10. A method of obtaining a positron emission image of a portion of a mammal, comprising the steps of:
    administering to a mammal a compound of claim 1; and
    acquiring a positron emission image of a portion of a mammal,
    wherein said portion of a mammal is the myocardium.

11. The method of claim 10 wherein the mammal is a human.

12. A method of imaging myocardial perfusion comprising:
    administering to a patient a compound of claim 1; and
    scanning the patient using diagnostic imaging.

* * * * *